(12) United States Patent
Cote

(10) Patent No.: US 6,228,271 B1
(45) Date of Patent: May 8, 2001

(54) METHOD AND INSTALLATION FOR IN SITU TESTING OF MEMBRANE INTEGRITY

(75) Inventor: M. Pierre Cote, Dundas (CA)

(73) Assignee: Omnium de Traitement et de Valorisation (OTV) (FR)

( * ) Notice: Subject to any disclaimer, the term of this patent is extended or adjusted under 35 U.S.C. 154(b) by 0 days.

(21) Appl. No.: 09/194,489

(22) PCT Filed: May 28, 1997

(86) PCT No.: PCT/FR97/00930

§ 371 Date: Jul. 19, 1999

§ 102(e) Date: Jul. 19, 1999

(87) PCT Pub. No.: WO97/45193

PCT Pub. Date: Dec. 4, 1997

(30) Foreign Application Priority Data

May 28, 1996 (FR) .................................................. 96 06780

(51) Int. Cl.[7] .................................................. G01M 03/04
(52) U.S. Cl. .................................. 210/739; 210/87; 73/38; 73/40
(58) Field of Search .................. 73/38, 40; 210/85, 210/87, 90, 739, 741

(56) References Cited

U.S. PATENT DOCUMENTS 5,353,630 * 10/1994 Soda et al. .

FOREIGN PATENT DOCUMENTS

| | | |
|---|---|---|
| 3312729A1 | 10/1983 | (DE) . |
| 3917856A1 | 12/1989 | (DE) . |
| 4421639A1 | 1/1996 | (DE) . |
| 064 159 A2 | 11/1982 | (EP) . |
| 0139 202 A1 | 5/1985 | (EP) . |
| 517 501 A2 | 12/1992 | (EP) . |
| 0592 066 A1 | 4/1994 | (EP) . |
| 2132366A | 7/1984 | (GB) . |
| 4-19541 * | 1/1992 | (JP) . |
| 7-60073 * | 3/1995 | (JP) . |

* cited by examiner

Primary Examiner—Joseph W. Drodge
Assistant Examiner—Terry K. Cecil
(74) Attorney, Agent, or Firm—Coats & Bennett, PLLC

(57) ABSTRACT

A process is described for testing the integrity of liquid filtration membranes without the use of pressurized air. The process includes draining the upstream compartment 3 and filling it with air by venting it to the atmosphere; applying a partial vacuum to the permeate compartment 4 to create a pressure difference across the membrane 2; and measuring the liquid flow out of the permeate chamber that corresponds to air passing through the leak orifices in the membrane. After stabilization of the pressure in the permeate chamber, the resulting constant liquid flow rate out of the permeate chamber is then used to evaluate the integrity of the membrane. An installation for implementing the process is also described and can include a plurality of filtration modules.

16 Claims, 2 Drawing Sheets

METHOD AND INSTALLATION FOR IN SITU TESTING OF MEMBRANE INTEGRITY

FIELD OF THE INVENTION

This invention relates to the domain of filtration processes and installations used for purification of liquids, particularly water, of the type including at least one filtration membrane.

The process and the installation according to the invention are preferably applied in the domain of water purification, for the production of drinking water. However, an expert in the subject could consider using the same principles for other types of treatment, or for the treatment of liquids other than water.

BACKGROUND OF THE INVENTION

The main objectives of water treatment in order to make it drinkable in accordance with the standards in force are as follows:
eliminate suspended solids,
eliminate organic materials,
eliminate unwanted ions,
sterilize.

Conventional treatment for achieving these objectives use a series of physicochemical steps including coagulation, flocculation, settlement, filtration, and usually oxidation.

The role of the filtration step, to which the invention relates particularly, is to disinfect treated water by retaining micro-organisms (viruses, bacteria and protozoa) contained in the water, and particularly pathogenic micro-organisms.

This membrane filtration step is advantageously carried out by means of organic membranes with variable size pore diameters depending on the size of the particles to be retained, and possibly with different configurations (hollow fibers, spiral modules, etc.).

Ultrafiltration and microfiltration with organic membranes are thus considered to be excellent methods of treating water and making it drinkable.

One of the main problems that arises with installation using membrane filtration is due to leaks that may occur in the membranes, significantly reducing their efficiency.

In practice, there are several potential sources of leaks in this type of installation using membranes, including particularly membrane imperfections, mechanical joints, joints and glue spots and membrane breakages. The problem of membrane breakages is more severe with membranes composed of hollow fibers that are relatively brittle.

Therefore in order to overcome this problem, particularly within the context of making water drinkable, it is essential to have processes capable of guaranteeing the integrity of membrane systems, and verifying that they do not leak. This type of process is intended to quickly locate leaks so that the defective elements responsible for the local leak can be repaired or replaced. It is essential that this type of process can be applied in situ, in other words directly on the filtration installation without needing to remove the filtration membranes.

The state-of-the-art includes several processes for achieving this objective.

Some processes simply consist of counting particles in the filtered liquid (permeate) in order to determine if the filtration operation is done correctly by the tested installation. In practice, if the number of particles found in the permeate is too high, it may be concluded that there is a leak in the installation. Although processes of this type are efficient, they have several disadvantages. Firstly, relatively sophisticated and expensive equipment necessary for particle counts has to be used. Secondly and especially, they have the disadvantage that they cannot be used on water with a low initial content of particles to be filtered.

Japanese patent application JP-A-H7024273 proposes to use a gas containing particles with a constant size at a constant concentration, to filter the gas in question through the membranes to be treated, and to detect particles on the permeate side. This technique has the disadvantage that a special fluid needs to be used, namely a gas containing particles with a constant composition, which increases the complexity and cost of the integrity test.

Japanese patent application JP-A-H7060073 purposes a technique consisting of installing a microfilter at the outlet of the main filtration installation, and from time to time measuring the pressure in this microfilter. Any pressure increase at the microfilter suggests that there must be a leak. The main disadvantage of this technique is that it requires the use of an additional filtration device that is relatively difficult to use and significantly increases the total cost of the installation.

Another method consists of using a hydrophore to detect noise resulting from the breakage of hollow fibres. However, this type of test can only detect leaks on membranes made with hollow fibers, in which air is used for backwashing.

Another suggestion in the state-of-the-art, and particularly in American patent application U.S. Pat. No. 5,353,630, suggests evaluating the integrity of filtration membranes using the bubble point principle. This measurement consists of wetting the membranes to be tested and submitting it to a gradually increasing air pressure until the air flushes the liquid through the leak orifices in the said membrane. By using test pressures between about 0.5 bars and 1 bar, it is thus possible to detect the presence of orifices with a size of the order of 1 micron corresponding to imperfections in the filter layer, leaking seals, broken hollow fibers, etc. The size of this type of leak orifice is considerably larger than the cutoff limits of tested membranes which are the order of 0.1 $\mu$m for microfiltration membranes, 0.001 $\mu$m for ultrafiltration membranes and even smaller for inverse osmosis.

The Young and Laplace equation can be used to estimate the sizes of these orifices allowing air to pass and thus determine whether or not there are any leaks in the membrane. According to this equation:

$$d = 4\gamma\, K_t \cos\theta / \Delta P$$

where d is the orifice diameter, $\gamma$ is the surface tension at the air-liquid interface, $K_t$ is a correction factor taking account of the tortuosity of the pores and which is typically equal to 0.2 to 0.3 for membranes made by phase inversion, $\Delta P$ is the bubble point, and $\gamma$ is the surface tension at the air-liquid interface. Note that when an air bubble penetrates into an orifice, the diameter of this bubble reaches the diameter of the orifice and therefore $\theta = 0$ and $\cos\theta = 1$.

U.S. Pat. No. 5,353,630 consists of applying air pressure to the upstream compartment delimited by the membrane and measuring the air flow representing the air flow passing through the membrane.

This technique has the disadvantage that the upstream compartment has to be pressurized, which leads to the need to equip the installation with means of supplying pressurized air. However means of pressurizing air are only present on some types of filtration installations, and particularly those that use backwashing of membranes by air.

SUMMARY OF THE INVENTION

The purpose of this invention is to propose a process for evaluating the integrity of filtration membranes without the disadvantages of the state-of-the-art.

In particular, one objective of the invention is to present a process of this type that uses the bubble measuring principle, without the use of pressurized air.

Another purpose of the invention is to describe a process of this type that can be used for any type of symmetric or asymmetric, composite or non-composite, ultrafiltration, microfiltration, nanofiltration or inverse osmosis membrane, and for any type of membrane configuration (hollow fibers, spiral modules, etc.).

Another purpose of the invention is to propose a process of this type that can easily be used for a set of membrane modules or for a given module.

These various purposes, and others which will become apparent later, are achieved by the invention that relates to a process for testing the integrity of at least one liquid filtration membrane, the said membrane delimiting an upstream compartment within a filtration device that collects the said liquid to be filtered, and a permeate compartment that collects the said filtered liquid, the said process being characterized in that it comprises steps consisting of:

- filling the said upstream compartment with air to bring it to atmospheric pressure $P_{atm}$ and applying a partial vacuum in the said permeate compartment in order to create a pressure difference between the said upstream compartment and the said permeate compartment;
- measuring the liquid flow corresponding to the air passing through leak orifices under the effect of the said pressure difference, and the pressure existing in the said permeate compartment;
- after stabilization of the pressure at a predetermined pressure $P_{test}$, and before all the liquid has drained out of the permeate compartment, measuring the corresponding constant liquid flow $Q_{test}$;
- evaluating the integrity of the membrane as a function of the measured flow $Q_{test}$.

Therefore, the principle of the invention is to monitor the variation of the pressure existing in the permeate compartment, and determine the liquid flow $Q_{test}$ corresponding to air passing through the membrane at a stable pressure $P_{test}$, this flow being representative of the membrane integrity.

Unlike the technique used in patent U.S. Pat. No. 5,353,630, the process according to the invention does not use pressurized air, but instead uses a partial vacuum. Thus it can be used for membrane filtration installations in which there is no means of generating pressurized air.

Furthermore, the process according to the invention uses the bubble point measurement principle by causing air to pass through the membrane when it is still wet, in the direction used for the filtration. This has the advantage that it does not embrittle the membrane being tested, and does not induce expansion that can damage the membrane, particularly in the case of asymmetric or composite membranes.

The pressure $P_{test}$ chosen for the test will be determined by the expert in the subject as a function of the membrane being tested, and will vary. In practice, this pressure will preferably be between 0.2 bars and 0.9 bars (absolute pressure). Note also that the liquid flow $Q_{test}$ at this pressure $P_{test}$ will be measured before all the liquid has drained out the compartment.

The process according to the invention measures a flow $Q_{test}$ that corresponds to the air that passes through the membrane and accumulates in the upper part of the permeate compartment, and can be used to evaluate the integrity of the membrane being tested starting from this measurement.

However, the process according to the invention preferably includes a correction of the measured flow $Q_{test}$, to enable a more precise evaluation of this integrity.

According to a first correction proposed by the invention, the flow $Q_{test}$ measured at pressure $P_{test}$ existing in the permeate compartment can be corrected for the real flow in orifices $Q_{orif}$ at the average pressure existing in the membrane $(P_{atm}+P_{test})/2$.

This air flow in the orifices is estimated as follows using the perfect gas law:

$$Q_{orif}=Q_{test}(P_{test}/(P_{atm}+P_{test}/2))$$

A second correction consists of correcting values for the test conditions to obtain values corresponding to filtration, which involves a conversion from air to liquid (viscosity correction) and a conversion from the cross-membrane test pressure $(P_{atm}-P_{test})$ to the cross-membrane filtration pressure $(\Delta P_{filt})$. This is done using Hagen-Poiseuille equation that describes laminar flow in a cylinder.

$$Q\mu/\Delta P=\pi d^4/128l$$

where Q is the flow in the cylinder, d is the diameter of the cylindrical orifice, $\Delta P$ is the pressure loss, $\mu$ is the viscosity and l is the cylinder length.

When applied to the test according to the invention, this equation gives:

$$Q_{orif}\mu_{air}/(P_{atm}-P_{test})=\pi d^4/128l$$

When applied to filtration, the same equation gives:

$$Q_{leak}\mu_{liquid}/\Delta P_{filt}=\pi d^4/128l$$

These two equations can be combined together:

$$Q_{leak}=Q_{orif}\mu_{air}\Delta P_{filt}/\mu_{liquid}|P_{atm}-P_{test}|$$

Replacing $Q_{orif}$ by its value above at the time of the first correction, an expression for $Q_{leak}$ is obtained expressed as a function of known variables:

$$Q_{leak}=Q_{test}\,(\mu_{air}^2\Delta P_{filt}P_{test})/(\mu_{liquid}(P_{atm}^2-P_{test}^2))$$

By defining $f_1=\mu_{liquid}/\mu_{air}$ and $f_2=(P_{atm}^2-P_{test}^2)/2\ \Delta P_{filt}$ $P_{test}$, $Q_{leak}$ can be obtained using the following equation:

$$Q_{leak}=Q_{test}/f_1f_2.$$

In which $f_1$ is an air-filtered liquid viscosity correction factor, and $f_2$ is a pressure correction factor. The value of the corrected leakage rate $Q_{leak}$ is preferably calculated within the process according to the invention.

Note that the method for correcting the flow $Q_{test}$ described above is in no way restrictive and an expert in the subject could consider correcting $Q_{test}$ according to any other process without going outside the framework of the invention.

Also preferably, the integrity of the membrane being tested is evaluated by calculating the logarithmic deterioration of the said membrane starting from the said leakage flow $Q_{leak}$ and the filtered flow $Q_{filt}$ on the said membrane, by using the following equation.

$$AL=\log_{10}(Q_{leak}/Q_{filt})$$

This calculation method is based on the assumption that all particles (e.g. micro-organisms) present in the leakage flow pass through the membrane, and all particles present in the filtered flow are stopped by the membrane. Preferably, the process according to the invention also includes a step that consists of calculating the diameter of membrane leak orifices as a function of the cross-membrane pressure by applying the equation $d=4\gamma K_t/\Delta P$ where $\gamma$, $\Delta P$ and $K_t$ are as defined above.

Furthermore, according to one interesting variant of the invention, the said step consisting of filling the said upstream compartment with air so that it is at atmospheric pressure is done by draining the said compartment. This preferred characteristic is particularly suitable for installations with immersed membranes, in which draining can quickly expose the filtrate side of the membranes to air. This is why the process according to the invention is advantageously used on this type of membrane, particularly membranes composed of hollow fibers.

When the process is used on an installation without any draining means, the membrane in the permeate compartment can be exposed to air by drawing in the free liquid present in this compartment using means of creating a partial vacuum in the permeate compartment.

According to one interesting variant of the invention, the process is used on several membranes or set of membranes in parallel, and when an integrity fault is observed at this stage, each of the said membranes or each of the said sets of membranes is tested afterwards in sequence in order to determine which of the said membrane or said act of membrane(s) has (have) an integrity fault.

The invention also relates to an installation for embodiment of the process described above, the said installation comprising at least one filtration device including at least one set of filtration membranes delimiting at least one upstream compartment containing a liquid to be filtered and at least one permeate compartment containing the said filtered liquid, and being characterized in that it comprises means of placing the said upstream compartment at atmospheric pressure, means of creating a partial vacuum in the said permeate compartment, means of measuring the pressure in the said permeate compartment and means of measuring the liquid flow corresponding to air passing through the said membrane.

Preferably, the installation according to the invention includes means of calculating the leakage flow and/or the logarithmic deterioration of the said membrane and/or the diameter of the leak orifices. These parameters are useful for determining the state of the membrane more precisely, as described above.

Also preferably, the said means of creating a partial vacuum in the permeate compartment include a least one pump equipped with means of regulating its flow to keep the pressure constant, advantageously such as a positive displacement pump.

Advantageously, the said membranes are immersed membranes with hollow fibers. As mentioned above, the process according to the invention is particularly easy to implement with this type of membrane.

Preferably the capacity of the said pump is defined as being a fraction (preferably $10^{-8}$ to $10^{-6}$) of the filtration flow through the membrane(s) being tested.

Advantageously, the said filtration device has means of draining the upstream compartment. As already mentioned, when used for installations with immersed membranes, this type of draining means can easily expose wet membranes to air. When the step consisting of applying atmospheric pressure to the upstream compartment cannot be done by draining this compartment, it may be done by drawing free liquid into the upstream compartment, using upstream means to create a partial vacuum in the permeate compartment, and providing an ambient air inlet in the upstream compartment.

According to one interesting variant of the invention, the said filtration device comprises several membrane modules, the said means of creating a partial vacuum and the said calculation means being common to the said modules, and selection means for using the means mentioned above either on all the said modules, or on only one, or several, of the said modules. In this way, the process according to the invention may be carried out globally on a set of membranes or membrane modules, and if the result at this stage is negative it will be possible to isolate one or several of these modules or one or several of these membranes in order to determine which elements are affected. For example, the selection means in question may be composed of a network of manual valves or solenoid valves.

BRIEF DESCRIPTION OF THE DRAWINGS

The invention and its various advantages will be more easily understood by means of the following description of a non-restrictive embodiment of the invention with references to the drawings in which.

DETAILED DESCRIPTION OF THE DRAWINGS

Figure 1:
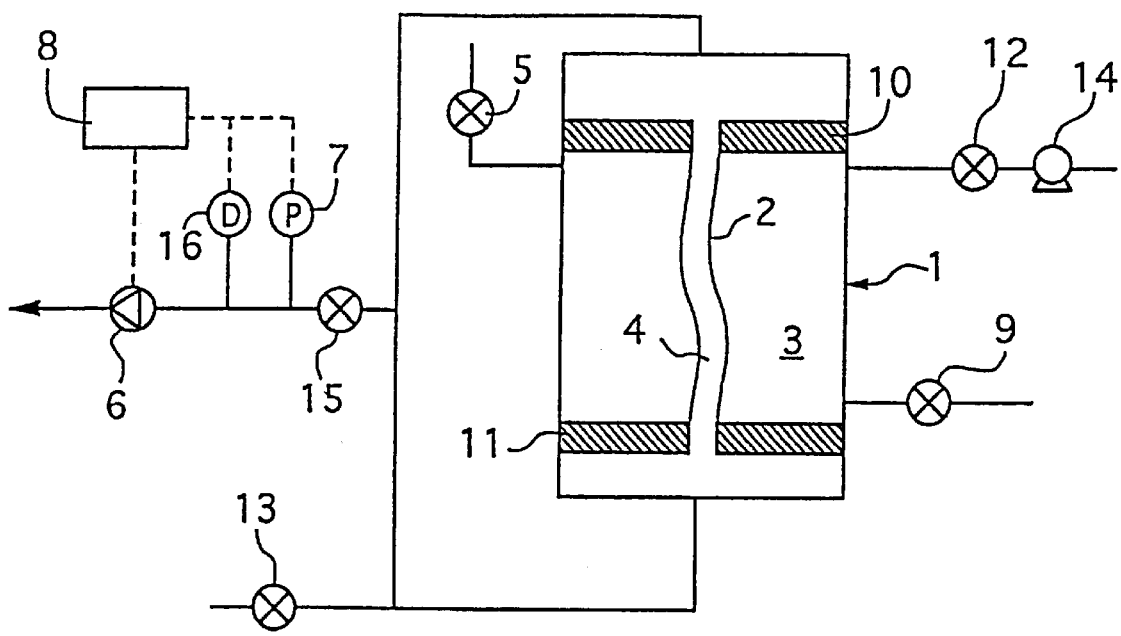
FIG. 1 is a diagram showing the principle of the process according to this invention.

With reference to FIG. 1, the process according to the invention is described in the context of a filtration installation including a membrane filtration device 1, and for reasons of clarity only showing a single membrane 2 composed of hollow fibers placed vertically in the said device, and only showing a single hollow fiber. Within the filtration device 1, this hollow fiber delimits firstly an upstream compartment 3 located outside the fiber and containing a liquid to be filtered, and secondly a permeate compartment 4 composed of the opening through the hollow fiber. Membrane 2 is isolated by glue joints 10, 11 provided in its upper part and its lower part respectively. Device 1 also comprises firstly means of feeding device 1 with liquid to be filtered connected directly to the upstream compartment 3, the said feed means being composed essentially of a valve 12 and a pump 14, and secondly means of drawing off the filtered liquid (permeate) connected directly to the permeate compartment 4, the said means consisting mainly of a valve 13.

The installation according to this invention comprises means 5 of putting the upstream compartment at atmospheric pressure, means 9 of draining this compartment, means 6 of creating a partial vacuum in the permeate compartment 4, means 7 (external manometer) of measuring the pressure existing in this compartment by a pressure sensor placed at mid-height of the set of membranes, means 16 (flow meter) of measuring the water flow corresponding to air passing through the membrane and means 8 of measuring the partial vacuum and of calculating the membrane leakage flow and its logarithmic deterioration making use of the recorded flow values.

Note that the flow meter 16 may be replaced by a measurement of the pump rotation speed.

The pressure existing in the permeate compartment may be read on the outside manometer 7. This manometer is located at mid-height of the set of membranes, and gives the pressure $P_{test}$ directly. Obviously, this manometer could also be placed in any other position, and $P_{test}$ could be obtained by a simple calculation.

Within the framework of this embodiment, means 9 consist of a simple drain valve placed in the lower part of the upstream compartment 3, means 5 consist of a valve placed in the upper part of the upstream compartment. The means of creating a partial vacuum in the upstream compartment advantageously use a positive displacement pump 6 used to obtain a constant pressure by varying its rotation speed. This pump is connected to the permeate compartment 4 through a duct on which a valve 15 is installed.

Filtration mode is stopped when the process according to the invention is being used. Consequently, the supply of liquid to be filtered is closed off by closing valves 12 and 13 and by stopping pump 14.

The upstream compartment 3 is then drained and vented to atmospheric pressure by opening valve 5 and 9 at the same time. Once the liquid to be filtered in this compartment has been drained and the compartment is at atmospheric pressure, valve 15 is opened a pump 6 is started up in order to create a partial vacuum in the permeate compartment 4 and an air passage through the leakage orifices may exist in the membrane under the effect of the difference in pressures in this permeate compartment 4 and in the upstream compartment 3. As will be explained in detail later, the pressure existing in this compartment gradually drops, until it reaches a predetermined value $P_{test}$. At the same time, the corresponding liquid flow gradually reduces until it reaches a leakage flow $Q_{test}$. Pressures and flows are measured continuously. When the approximately constant leakage flow $Q_{test}$ is measured at pressure $P_{test}$, this data is sent to the calculation means 8 used to calculate the leakage flow corrected as a function of the pressure and viscosity, and the membrane deterioration. The calculation means include means of inputting parameters and constants necessary for these calculations.

Figure 2:
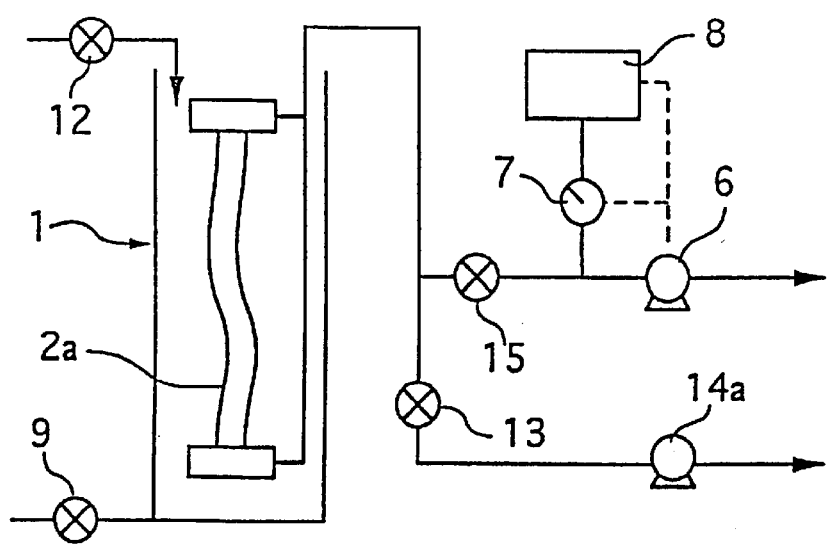
FIG. 2 shows a water filtration installation with immersed membranes according to the invention.

Another immersed membrane water filtration installation is shown in FIG. 2. In this type of installation, the water is not fed under pressure, and instead the permeate is drawn out using a pump 14a. (Structural elements common to FIGS. 1 and 2 are referenced with the same references). This figure shows the membranes in the form of a filtration module 2a composed of several membranes directly immersed in the liquid to be filtrated. In filtration mode, the permeate is evacuated both through the top and bottom of the modules. In this embodiment, the filtration module 2a is composed of immersed ZeeWeed membranes (registered trademark of Zenon Environmental Inc., Burlington, Canada) with a filtration surface area of 13.9 m$^2$ and a height of 1.80 m. Finally, note that the means of measuring the water flow in the installation described with reference to FIG. 1 corresponding to the air passing through the membrane, are replaced by a measurement of the pump rotation speed.

The integrity of the membranes in the installation shown in FIG. 2 was tested according to the invention.

An operation input the following parameters into the calculation means 8 during this test:

| | |
|---|---|
| Membrane height | 1.80 m |
| Atmospheric pressure $P_{atm}$ | 1.01 bars |
| Absolute pressure $P_{test}$ reached during the test corrected to the center of the set of membranes | 0.61 bars |
| Leakage flow $Q_{test}$ measured during the test | 42 l/h |
| Surface tension at the water-air interface $\gamma$ | 0.0723 N/m |
| Membrane correction factor $K_c$ | 0.25 |
| Air viscosity $\mu_{air}$ | 0.0182 cP |
| Water viscosity $\mu_{water}$ | 1.0019 cP |

-continued

| | |
|---|---|
| Filtration flow | 700 l/h |
| The average cross-membrane filtration pressure ($\Delta P$) | 0.4 bars |

Figure 3:
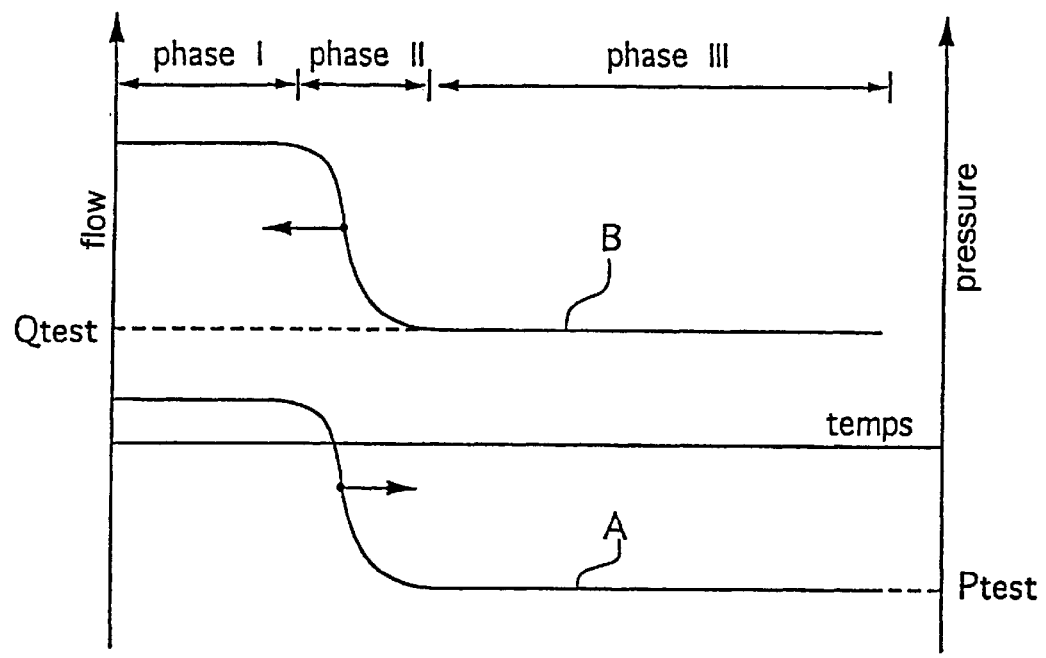
FIG. 3 shows the variation of the flow and pressure existing in the permeate compartment during use of the process according to the invention.

Curve A in FIG. 3 shows the variation with time of the pressure existing in the permeate compartment during the test, and curve B shows the corresponding flow variation with time.

Curves A and B both have three main phases I, II and III as shown in FIG. 3.

Phase I at the beginning of the test is when free water is evacuated at a pressure close to static pressure. This phase is short in this embodiment since there is not very much free water in the upstream compartment, since this water has almost all been removed by the drainage means. However in other embodiments, when this face water cannot be drained, the free water will be removed using the pump provided to create a partial vacuum in the permeate compartment. Phase I will then be much longer.

The negative pressure created by pump 6 during phase II contracts the membrane, which as the effect of quickly reducing the flow.

Finally during phase III, the pressure inside the permeate compartment stabilizes at the value chosen for the test and the measured flow $Q_{test}$ corresponds to leaks through orifices that allow air to pass. In this embodiment, the pressure $P_{test}$ was fixed at 0.61 bars and the measured water flow was 42 l/h. These data were input in the calculation means 8 as described above.

The parameters input in the calculation means 8 were used to determine the diameter of the orifices through which air passes, the corrected leakage flow and the logarithmic deterioration of the membrane.

Calculation of leak orifice diameters

These diameters were evaluated using the following equation:

$$d = 4\gamma\, K_t/\Delta P$$

where $\gamma$ is the surface tension at the air-liquid interface, $\Delta P$ is the cross-membrane pressure and $K_t$ is a correction factor representing the tortuosity of pores in the said membranes.

The cross-membrane pressure was calculated for the top of the membrane and for the bottom of the membrane considering that the height of the membrane is 1.80 m and the average cross-membrane pressure is 0.4 bars. This calculation leads to a cross-membrane pressure at the top of the membrane equal to 0.31 bars and a cross-membrane pressure equal to 0.49 bars corresponding to leak orifice of 1.5 μm and 2.3 μm respectively.

Calculation of the corrected leakage flow $Q_{leak}$

This corrected leak was determined from the measured flow $Q_{test}$ which was recorded as 42 l/h.

Correction factors $f_2$ and $f_1$ were determined using the equations given above, and the following results were obtained:

Viscosity correction factor $f_1$:

$f_1 = \mu_{water}/\mu_{air} = 1.009/0.0182 = 55$ pressure correction factor $f_2$:

$f_2 = (P_{atm}^{\,1} - P_{test}^{\,2})/2\Delta P_{test} P_{test} = (1.01^1 - 0.61^2)/2 \times 0.40 \times 0.61 = 1.33$ The equation $Q_{leak} = Q_{test}/f_1\, f_2$ was then used by the calculation means and the values $Q_{leak} = 0.575$ l/h was obtained.

Calculation of the logarithmic deterioration AL of the membrane

The equation $Al=\log_{20}(Q_{leak}/Q_{filt})$ was used by the calculation means and the value AL=3.1 was obtained.

Figure 4:
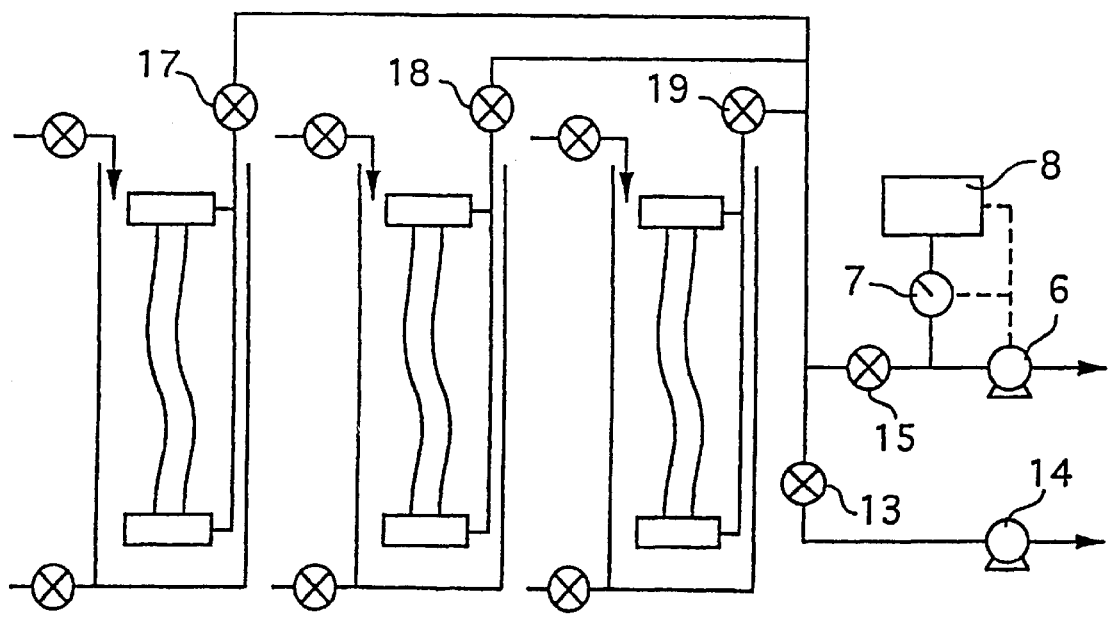
FIG. 4 shows another embodiment of an installation according to the invention.

Another embodiment of the installation according to the invention is shown in FIG. 4, the said installation comprising three filtration modules identical to that in FIG. 1. The installation also comprises a pump 6, water flow measurement means 7 and calculation means 8 common to the three modules. Each module is equipped with a pressure sensor to determine the pressure in its permeate compartment and connected to calculation means 8.

Finally, the selection means consisting of a network of valves 15, 17, 18, 19, make it possible to put means 6, 7, 8 in communication with all modules or with only one of them. This type of arrangement makes it possible to use the process according to the invention firstly for all module and secondly, if an integrity fault is determined at this stage, for only one of the modules in order to determine which module(s) is (are) actually defective.

The embodiments of the invention described herein are not intended to reduce the scope of the invention. Many modifications may be made to them without going outside its scope as defined by the claims. In particular these modifications may concern the membrane type, their configuration and obviously the pressures used.

What is claimed is:

1. Process for testing the integrity of at least one liquid filtration membrane, said membrane delimiting an upstream compartment within a filtration device that collects liquid to be filtered, and a permeate compartment that collects filtered liquid, said process comprising the steps of:

a. draining said upstream compartment of liquid and filling said upstream compartment with air by venting it to atmospheric pressure ($P_{atm}$), said permeate compartment having filtered liquid therein;

b. applying a partial vacuum to said permeate compartment to create a cross-membrane pressure difference between said upstream compartment and said permeate compartment;

c. measuring liquid flow out of said permeate chamber that corresponds to air passing through leak orifices in said membranes under the effect of said cross-membrane pressure difference and the pressure existing in said permeate compartment;

d. after stabilization of the pressure in said permeate chamber at a predetermined pressure ($P_{test}$) and before all the liquid has drained out of the permeate compartment, measuring a constant liquid flow out of the permeate chamber ($Q_{test}$) that corresponds to said stabilized pressure; and e. evaluating the integrity of the membrane as a function of the measured liquid flow ($Q_{test}$).

2. Process according to claim 1, wherein said predetermined pressure ($P_{test}$) is between about 0.2 bars and 0.9 bars (absolute pressure).

3. Process according to claim 1, wherein said evaluating step includes correcting the measured liquid flow ($Q_{test}$) by applying the equation $Q_{leak}=Q_{test}/f_1 f_2$, wherein $Q_{leak}$ is leakage flow through the membrane, $f_1$ is an air viscosity-filtered liquid viscosity correction factor, and $f_2$ is a pressure correction factor.

4. Process according to claim 3, wherein said evaluating step includes calculating the logarithmic deterioration (AL) of the membrane using the equation $Al=\log 10(Q_{leak}/Q_{filt})$, where $Q_{filt}$ is filtered flow through the membrane.

5. Process according to claim 1, including the step of calculating the diameter (d) of the leak orifices as a function of the cross-membrane pressure difference by applying the equation $d=4\gamma K_t/\Delta P$, where $\gamma$ is the surface tension at the air-liquid interface, $K_t$ is a correction factor representing tortuosity of pores of said membrane and $\Delta P$ is the cross-membrane pressure difference.

6. Process according to claim 1, wherein said membrane is an immersed membrane comprising hollow fibers.

7. Process according to claim 6, wherein said step of filling said upstream compartment with air is carried out by draining said upstream compartment.

8. Process according to claim 1, wherein said step of filling said upstream compartment with air is carried out by drawing in free liquid into said upstream compartment using upstream means in order to create a partial vacuum in said permeate compartment and by providing an ambient air inlet in said upstream compartment.

9. Process according to claim 1, wherein said at least one membrane comprises a plurality of membranes or sets of membranes in parallel, and after an integrity defect has been found, said process including the step of testing each of said membranes or at least one membrane of each of said sets of membranes in turn in order to determine which of said membranes or said sets has an integrity defect.

10. An installation for implementing said process according to claim 1, said installation comprising: at least one filtration device having at least one filtration membrane delimiting at least one upstream compartment containing the liquid to be filtered and at least one permeate compartment containing the filtered liquid, means for venting said at least one upstream compartment to atmospheric pressure, means for creating a partial vacuum in said at least one permeate compartment, means for measuring the pressure in said at least one permeate compartment, and means for measuring the flow corresponding to air pressure through said at least one filtration membrane.

11. Installation according to claim 10, including means for calculating at least one of: leakage flow through said membrane, logarithmic deterioration (AL) of said membrane, and the diameter of leak orifices in said membrane.

12. Installation according to claim 11, wherein said filtration device comprises a plurality of membrane modules and wherein said means for creating a partial vacuum, said means for measuring flow and said means for calculating are common to all of said plurality of membrane modules, and further comprising a means for selecting at least one of said membrane modules to be subject to each of said means for creating a partial vacuum, means for measuring flow and means for calculating.

13. Installation according to claim 10, wherein said means for creating a partial vacuum in said at least one permeate compartment comprises at least one pump equipped with means for regulating liquid flow to keep pressure constant in said at least one permeate compartment.

14. Installation according to claim 13, where the capacity of said at least one pump is defined as a fraction of the filtration flow through said at least one filtration membrane being tested.

15. Installation according to claim 10, wherein said at least one filtration membrane is an immersed membrane comprising hollow fibers.

16. Installation according to claim 15, wherein said at least one filtration device comprises a means for draining said at least one upstream compartment.

* * * * *